United States Patent
Hegmans et al.

(10) Patent No.: US 11,278,605 B2
(45) Date of Patent: *Mar. 22, 2022

(54) METHOD FOR PREPARING AN IMMUNOGENIC LYSATE, THE LYSATE OBTAINED, DENDRITIC CELLS LOADED WITH SUCH LYSATE AND A PHARMACEUTICAL COMPOSITION COMPRISING THE LYSATE OR THE DENDRITIC CELLS

(71) Applicant: Amphera B.V., 's-Hertogenbosch (NL)

(72) Inventors: Josephus Petrus Johannes Jacobus Hegmans, Rotterdam (NL); Joan Geertrudis Jacobus Victor Aerts, Steenbergen (NL)

(73) Assignee: AMPHERA B.V., 'S Hertogenbosch (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,072

(22) Filed: Apr. 3, 2018

(65) Prior Publication Data

US 2018/0296654 A1 Oct. 18, 2018

Related U.S. Application Data

(63) Continuation of application No. 14/758,153, filed as application No. PCT/EP2013/077837 on Dec. 20, 2013, now Pat. No. 9,962,433.

(30) Foreign Application Priority Data

Dec. 28, 2012 (NL) ..................... 2010067

(51) Int. Cl.
*A61K 39/00* (2006.01)
*C12N 5/0784* (2010.01)

(52) U.S. Cl.
CPC ........ *A61K 39/0011* (2013.01); *C12N 5/0639* (2013.01); *A61K 2039/5152* (2013.01); *A61K 2039/5154* (2013.01); *A61K 2039/5158* (2013.01); *A61K 2039/6043* (2013.01); *C12N 2501/052* (2013.01); *C12N 2501/22* (2013.01)

(58) Field of Classification Search
CPC .. A61K 2039/5152; A61K 45/06; A61P 35/00
See application file for complete search history.

(56) References Cited

U.S. PATENT DOCUMENTS

2002/0006413 A1 1/2002 Sobol et al.
2002/0176845 A1* 11/2002 Falkenberg ........ A61K 39/0011
424/85.1
2010/0303868 A1* 12/2010 Salazar Onfray ....... A61P 37/04
424/277.1

FOREIGN PATENT DOCUMENTS

WO WO-2008/005859 A2 1/2008

OTHER PUBLICATIONS

Fischer et al (Journal of Cancer Therapy, 2012, vol. 3, pp. 47-56) (Year: 2012).*
Mitchell et al (Annals of the New York Academy of Sciences, 1993, vol. 690, pp. 153-166) (Year: 1993).*
Veltman et al (BMC Cancer, 2010, vol. 10:464, 13 pages) (Year: 2010).*
Chalmers, et al. "Resistance of Human Melanoma Cells to Ultraviolet Radiation" Cancer Research (1976) vol. 36, pp. 1930-1934.
Ebstein, et al. "Cytotoxic T Cell Responses against Mesothelioma byApoptotic Cell-pulsed Dendritic Cells", American Journal of Respiration and Critical Care Medicine (2004), vol. 169, pp. 1322-1330.
Hegmans et al., "Immunotherapy of murine malignant mesothelioma using tumor lysate-pulsated dendritic cells", American Journal of Respiratory and Critical Care Medicine, 2005, vol. 171, pp. 1168-1177.
Hegmans, Joost P. et al., "Consolidative dendritic cell-based immunotherapy elicits cytotoxicity against malignant mesothelioma", American Journal of Respiratory and Critical Care Medicine, vol. 181, No. 12, Jun. 15, 2010, pp. 1383-1390.
International Search Report of PCT/EP2013/077837 dated Feb. 17, 2014.
Salucci, et al. "Ultraviolet B (UVB) Irradiation-Induced Apoptosis in Various Cell Lineages in Vitro", International Journal of Molecular Sciences (2013) vol. 14, pp. 532-546.
Shi, H. et al., "Hyperthermia enhances CTL cross-priming", The Journal of Immunology, The American Association of Immunologists, US, vol. 176, No. 4, Feb. 15, 2006, pp. 2134-2141.

* cited by examiner

*Primary Examiner* — Karen A. Canella
(74) *Attorney, Agent, or Firm* — Sunit Talapatra; Foley & Lardner LLP (57) ABSTRACT

The present invention relates to a method for the preparation of an immunogenic lysate from mesothelioma tumor cells, to such a lysate and to dendritic cells loaded with the lysate, the present invention further relates a pharmaceutical composition comprising such lysate or dendritic cells, to the use of the lysate, and to said loaded dendritic cells or said pharmaceutical composition for use in the prevention or treatment of mesothelioma.

12 Claims, 2 Drawing Sheets

METHOD FOR PREPARING AN IMMUNOGENIC LYSATE, THE LYSATE OBTAINED, DENDRITIC CELLS LOADED WITH SUCH LYSATE AND A PHARMACEUTICAL COMPOSITION COMPRISING THE LYSATE OR THE DENDRITIC CELLS

CROSS-REFERENCE TO RELATED APPLICATIONS

This application is a Continuation of U.S. patent application Ser. No. 14/758,153, filed Jun. 26, 2015, which is the National Phase of International Patent Application No. PCT/EP2013/077837, filed Dec. 20, 2013, published on Jul. 3, 2014 as WO 2014/102220 A1, which claims priority to Netherlands Application No. 2010067, filed Dec. 28, 2012. The contents of these applications are herein incorporated by reference in their entirety.

FIELD OF THE INVENTION

The present invention relates to a method for the preparation of an immunogenic lysate from mesothelioma tumor cells, to such a lysate and to dendritic cells loaded with the lysate. Furthermore, the invention provides a pharmaceutical composition comprising such lysate or dendritic cells. Moreover, the invention further provides the use of the lysate, the dendritic cells or the pharmaceutical composition in the prevention or treatment of mesothelioma.

BACKGROUND OF THE INVENTION

Malignant mesothelioma of the pleural cavity is a highly lethal neoplasm. With median survival durations of 9-15 months from the onset of symptoms, the prognosis is poor. To date, there is no standard curative therapy for malignant pleural mesothelioma (hereinafter: mesothelioma). Surgical approaches such as pleurectomy and extrapleural pneumonectomy result in high local recurrence rates and questionable survival benefit. The only treatment approved by the US Food and Drug Administration (FDA) is pemetrexed (Alimta)/cisplatin and has a median survival benefit of three months. Because of the limited success of current treatments, novel therapeutic regimens are urgently needed. The potential to harness the potency and the specificity of the immune system underlies the growing interest in cancer immunotherapy. One approach to activate the patient's immune system uses dendritic cells to present tumor-associated antigens and thereby generating anti-tumor specific responses.

Dendritic cells are highly mobile and extremely potent antigen presenting cells located at strategic places where the body comes in contact with its environment. In these locations they pick up antigens and transport them to the secondary lymphoid organs where they instruct and control activation of natural killer cells, B and T-lymphocytes, and efficiently activate them against the antigens [1]. This property makes them attractive candidates for use in therapeutic strategies against cancer [2-3]. Dendritic cells can be generated in large numbers in vitro; bypassing antigen presentation deficiencies caused by the immune suppressing tumor environment [4-7], and can subsequently be injected in a mature state to induce anti-tumoral responses [8-11].

Dendritic cell based immunotherapy has been found to induce protective and anti-tumor immunity in experimental animals and in some cancers in humans e.g. renal cell carcinoma, melanoma, glioma and lung cancer [12]. This has also been proven for mesothelioma. It has particularly been found that dendritic cell based immunotherapy had a beneficial effect on survival and reducing tumor growth in a mouse model for malignant mesothelioma [13].

Based on these preclinical findings in laboratory animals, a clinical trial was initiated to address the safety and feasibility of pulsed dendritic cells to induce tumor-specific cytotoxic T-cell responses in mesothelioma patients [14]. Ten patients were treated with chemotherapy (pemetrexed/cisplatin) followed by three vaccinations of autologous tumor lysate-loaded monocyte-derived dendritic cells. Chemotherapy was given prior to dendritic cell vaccination in order to reduce tumor load, thereby potentially augmenting the efficacy of the vaccination, as was earlier found in mice. From this study it became clear that injection of autologous tumor lysate-pulsed dendritic cells in mesothelioma patients after chemotherapy was safe and well tolerated.

However, using autologous tumor cell lysate to load dendritic cells has certain theoretical and practical disadvantages. A key problem associated with the autologous approach is that the number of tumor cells from resected tumor material of thoracic malignancies, in particular mesothelioma (either pleural fluid or biopsy) is very limited. As an example, in the first human clinical trial with dendritic cell based immunotherapy in mesothelioma, most patients were excluded from participation [14]. From a total number of 57 mesothelioma patients only ten patients were able to provide enough tumor material, although all patients had high tumor burden on CT/MRI scan.

Furthermore, autologous tumor material obtained from patients suffering from mesothelioma is very divers in total tumor amount and "contamination" with other cells. This results in highly variable tumor cell lysates making standardization extremely difficult. When such tumor material is loaded onto autologous dendritic cells different outcomes of the phenotype and stimulatory capacity are awaited. Moreover, preparing the autologous tumor material for each individual patient is time consuming and laborious. Also, quality tests are needed on each patient's lysate batch, making the procedure of dendritic cell based immunotherapy with autologous tumor lysate very expensive.

Another limitation associated with the use of autologous mesothelioma tumor cells, is the difficulty of in vitro manipulation of tumor derived cells. Different approaches to optimally prepare tumor cell derivatives (apoptotic or necrotic fragments), increasing the immunogenicity or enrichment by protein fractionation, and other important steps to increase efficacy, cannot be performed directly on autologous tumor material. Culturing autologous cells ex-vivo, until the number of cells is adequate for manipulation, is not an option for reasons that even short term culture of mesothelioma cells mostly failed to produce cell lines. Another reason why using autologous tumor cells is not feasible is the fact that relatively long culture periods are needed, during which the patient's disease progresses further.

In the prior art it has been suggested to use apoptotic allogeneic mesothelioma tumor cells for loading autologous dendritic cells. In this regard reference is made to the article of Ebstein et al, 2003, in the American Journal of Respiration and Critical Care Medicine. In this article intact apoptotic allogeneic mesothelioma tumor cells derived from one cell line are used in an in vitro study wherein autologous dendritic cells are loaded with said intact apoptotic tumor cells.

Although it was shown in this study that dendritic cells fed with apoptotic heat shock protein over-expressing mesothelioma tumor cells induced a cytotoxic T cell response, the method and cells used by Ebstein are not clinically useable. The cells used by Ebstein originate from one cell-line, consequently the antigens provided to the dendritic cells will be relatively limited and would thus seriously reduce it clinical use. This is also exemplified by the fact that the cell-lines used only show a positive result if the tumor cells have been subjected to a prior heat-shock treatment. More importantly, Ebstein uses intact tumor cells which have only been treated with UV-B to induce apoptosis. Since many cells may survive such an UV-B treatment, they are unsuitable for administration to patients. In this regard reference is made to Chalmers A. H. et al., 1976, in Cancer Research and to Salucci S. et al., 2013, in International Journal of Molecular Sciences.

Hence, a need remains for the provision of a safe and reliable method for treating patients suffering from mesothelioma and for the provision of medicaments and pharmaceutical compositions for use in the prevention or treatment of mesothelioma.

DETAILED DESCRIPTION OF THE INVENTION

A first aspect of the present invention relates to a method for the preparation of an immunogenic lysate comprising the steps of:
i) providing allogeneic mesothelioma tumor cells from at least two different cell lines;
ii) inducing necrosis or apoptosis in the tumor cells;
iii) lysing the necrotic or apoptotic tumor cells, such that a lysate is obtained.

With the method of the present invention, for the first time, allogeneic mesothelioma tumor cells originating from at least two different cell lines, have been used for preparing a lysate that can be used in the immunotherapy of patients suffering, or persons having an increased risk of developing mesothelioma.

Because differential antigen expression takes place in different mesothelioma tumor cell lines found in patients, it is not sufficient to provide dendritic cells loaded with antigens derived from only one cell line to a group of patients. Instead it is of importance to load the dendritic cells with sufficient tumor antigen sources, such that cytotoxic T-cell responses are induced against a large variety of mesothelioma tumors.

With the present invention this is achieved by loading the dendritic cells with a lysate of allogeneic mesothelioma tumor cells from at least two different cell-lines. By using different cell-lines multiple antigens are thus present in the lysate, which lysate may be used to load dendritic cells. This way, the chances are reduced that a mesothelioma tumor in a patient escapes by down-regulating a specific antigen.

Furthermore, the use of a lysate of said tumor cells for loading the dendritic cells is essential for the present invention. Due to the use of a lysate of the tumor cells a better mixing of the different antigens from the different tumor cell-lines can be achieved. This way, dendritic cells loaded with said lysate are able to present all the antigens from the different tumor cell-lines. This is not possible with intact (allogeneic tumor cells). Another advantage of using a lysate is that it is easier to produce in large quantities, that it is more easy to handle and package and that its quality can be monitored relatively easy.

In the context of the present invention the term "mesothelioma tumor cells" refers to cells derived from malignant mesothelioma.

In the context of the present invention the term "allogeneic" has its normal scientific meaning and refers to tumor cells which are derived from an individual which is different from the individual to which the lysate resulting from the method according to the present invention shall be later administered. The use of tumor cell lysates from allogeneic mesothelioma tumor cells provides a more standardized and easier approach, bypassing the need for an individually prepared autologous tumor lysate. It also creates opportunities to select the optimal source (apoptotic or necrotic), dose and delivery onto dendritic cells or perform manipulations to increase the immunogenicity of the cells. The utilization of a robust and validated large scale manufacturing process also requires fewer product batches for quality control tests such as identity, purity, quantity and sterility/safety testing. A major advantage of the allogeneic approach over autologous is that the tumor cell cells can be optimized, stored in bulk, and manufacturing/quality control timeliness shall not impact on the immediate disease progression of the patient as supply already exists.

In accordance with the present invention the term "necrosis" has its normal scientific meaning and means morphological changes of cells. Necrosis is, inter alia, characterized for example by "leakiness" of the cell membrane, i.e. an increased permeability which also leads to an efflux of the cell's contents and an influx of substances perturbing homeostasis and ion equilibrium of the cell, DNA fragmentation and, finally, to the generation of granular structures originating from collapsed cells, i.e. cellular debris. Typically, necrosis results in the secretion of proteins into the surrounding which, when occurring in vivo, leads to a pro-inflammatory response.

Methods for the determination whether a cell is necrotic are known in the prior art. It is not important which method the person skilled in the art chooses since various methods are known.

Necrotic cells in accordance with the present invention can be determined, e.g., by light-, fluorescence or electron microscopy techniques, using, e.g., the classical staining with trypan blue, whereby the necrotic cells take up the dye and, thus, are stained blue, or distinguish necrotic cells via morphological changes including loss of membrane integrity, disintegration of organelles and/or flocculation of chromatin. Other methods include flow cytometry, e.g., by staining necrotic cells with propidium iodide.

In accordance with the present invention the term "apoptosis" has its normal scientific meaning and means programmed cell death. If cells are apoptotic various changes in the cell occur, such as cell shrinkage, nuclear fragmentation, chromatin condensation, and chromosomal DNA fragmentation.

Apoptotic cells can be determined, e.g., via flow-cytometric methods, e.g., attaining with Annexin V-FITC, with the fluorochrome: Flura-red, Quin-2, with 7-amino-actinomycin D (7-AAD), decrease of the accumulation of Rhodamine 123, detection of DNA fragmentation by endonucleases: TUNEL-method (terminal deoxynucleotidyl transferase caused X-UTP nick labelling), via light microscopy by staining with Hoechst 33258 dye, via Western blot analysis, e.g., by detecting caspase 3 activity by labelling the 89 kDa product with a specific antibody or by detecting the efflux of cytochrome C by labelling with a specific antibody, or via agarose gel DNA-analysis detecting the characteristic DNA-fragmentation by a specific DNA-ladder.

In accordance with the present invention the term "lysing" relates to various methods known in the art for opening/destroying cells. In principle any method that can achieve lysis of the tumor cells may be employed. An appropriate one can be chosen by the person skilled in the art, e.g. opening/destruction of cells can be done enzymatically, chemically or physically. Examples of enzymes and enzyme cocktails that can be used for lysing the tumor cells are proteases, like proteinase K, lipases or glycosidases non-limiting examples for chemicals are ionophores, like nigromycin, detergents, like sodium dodecyl sulfate, acids or bases; and non-limiting examples of physical means are high pressure, like French pressing, osmolarity, temperature, like heat or cold. A preferred way of lysing cells is subjecting the cells to freezing and thawing. Additionally, a method employing an appropriate combination of an enzyme other than the proteolytic enzyme, an acid, a base and the like may also be utilized.

According to the present invention the term "lysate" means an aqueous solution or suspension comprising the cellular proteins and factors produced by lysis of tumor cells. Such a lysate may comprise macromolecules, like DNA, RNA, proteins, peptides, carbohydrates, lipids and the like and/or micromolecules, like amino acids, sugars, lipid acids and the like, or fractions from the lysed cells. The cellular fragments present in such a lysate may be of smooth or granular structure. Preferably, said aqueous medium is water, physiological saline, or a buffer solution.

The lysate according to the present invention is not limited to lysed necrotic cells. For example, due to the different sensitivity of the treated cells or due to the applied conditions, such as UVB radiation, also lysed apoptotic cells can form or be part of the lysate.

The term lysate as used herein also encompasses preparations or fractions prepared or obtained from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other protein chemical, molecular biological, biochemical, immunological, chemical or physical methods to separate above components of the lysates. In a preferred embodiment those fractions which are more immunogenic than others are preferred. Those skilled in the art are able to choose a suitable method and determine its immunogenic potential by referring to the above general explanations and specific explanations in the examples herein, and appropriately modifying or altering those methods, if necessary.

Preferably, the immunogenicity of the mesothelioma tumor cells, is enhanced before inducing necrosis or apoptosis in the tumor cells. This increase of the immunogenicity can be achieved by incubating the allogeneic tumor cells at 41.2° C. or higher for 1-120 minutes, preferably 20-50 minutes, most preferably about 30 minutes. Another way to increase the immunogenicity of the tumor cells is to expose them to oxidative modification, for example by subjecting the cells to hypochlorous acid or to hydrogenperoxide. The immunogenicity of the allogeneic tumor cells can also be enhanced by exposing the cells to a histone deacetylase inhibitor, such as valproic acid or suberoylanilide hydroxamic acid, or by subjecting the tumor cells to DNA-methyltransferase inhibitors, such as 5-aza-2-deoxycytidine.

The mesothelioma tumor cells, are preferably derived from vertebrates, preferably from a mammal, most preferably from humans.

In order to obtain a good immunogenic response it is preferred to use a mixture of allogeneic mesothelioma tumor cells, from at least two mesothelioma tumor cell-lines, preferably at least three mesothelioma tumor cell-lines, for preparing the lysate. Particularly good results are obtained when a mixture of at least five mesothelioma tumor cell lines, is used for preparing the lysate. Using such mixtures of cell lines as a source of tumor lysate is advantageous in providing a broader antigenic repertoire of tumor associated antigens (wide variety of potential tumor antigens), which will increase the ability of immune responses to recognize and destroy tumor cells because the opportunities to escape immune surveillance by modulation of antigen expression are more limited.

Preferably, at least one of the cell-lines used has been derived from a tumor tissue specimen with an immune contexture having:

more than 500 $CD3^+$ cells per $mm^2$;
more than 200 $CD45RO^+$ cells per $mm^2$;
less than 50 $FoxP3^+$ cells per $mm^2$; and
less than 1000 $CD206^+$ cells per $mm^2$.

Due to the presence of a relatively high amount of CD3 positive and CD45RO positive cells, it is clear that the tumor tissue specimen has been subjected to a high infiltration of CD3+ T cells and CD45RO memory T cells. In various cancers this is associated with a longer overall survival, this is also true for mesothelioma.

Furthermore, due to the relatively low amount of FoxP3 positive cells and CD206 positive cells it is clear that a high infiltration of regulatory T-cells and M2 macrophages has not taken place. This is also associated with a higher overall survival rate. The mesothelioma cell-line derived from this kind of tumor tissue specimens thus show a high immunostimulation, i.e. they provide sufficient amount of antigens, whereas they trigger little reaction of regulatory T-cells. In this regard reference is made to Fridman et al., 2012, in Nature Reviews Cancer and Galon et al., 2013, in the Journal of Pathology.

In view of the above, it is thus preferred to use a lysate prepared from such a cell-line in immunotherapy, in particular for pulsing dendritic cells. Lysate prepared from these tumor cells contain antigens that activate the immune system while tumor-derived suppressive factors are limited.

It is particularly preferred to use at least two of such cell-lines for preparing the lysate according to the present invention.

Within the context of the present invention the term "immune contexture" as used herein has its conventional meaning and refers to density of different immune cell populations in specimens of (human) tumors.

The density of the different immune cells is typically determined by means of histological staining of the samples. Methods for histologically staining immune cells with respect to CD3, CD45RO, FoxP3 and CD206 is commonly known in the art. In this regard reference is made to Fridman et al., 2012, in Nature Reviews Cancer which document is herewith incorporated by reference.

The allogeneic mesothelioma tumor cells, used in the method of the present invention are cultured in for example culture flasks. Due to the fact that these allogeneic cells have the ability to divide unlimited with minimal loss of their immunogenic properties, in contrast to non-cancerous cells, they are suitable to use for preparing the lysate.

Presently six human mesothelioma cell lines have been developed that provide particularly good results. These cell lines have been deposited at "Deutsche Sammlung von Mikro-organismen und Zellkulturen" in Germany, hereinafter DSMZ. The cell lines were given the following codes and accession numbers: Thorr 01 (deposit No. DSM ACC3191), Thorr 02 (deposit No. DSM ACC3192), Thorr 03 (deposit No. DSM ACC3193), Thorr 04 (deposit No. DSM ACC3194), Thorr 05 (deposit No. DSM ACC3195), Thorr 06 (deposit No. DSM ACC3196). The deposit were made pursuant to the terms of the Budapest treaty on the international recognition of the deposit of micro-organisms for purposes of patent procedure on Dec. 19, 2012 with Leibniz-Institut DSMZ-Deutsche Sammlung von Mikrooganismen und Zellkulturen GmbH (Inhoffenstrasse 7B, 38124, Braunschweig, Germany.

The cell-lines Thorr03 and Thorr02 are particularly noteworthy. These cell-lines have been derived from mesothelioma tumor specimens which showed a relatively high infiltration of CD3+ T cells and CD45RO memory T cells (i.e. a high immunostimulation). Moreover, these tumor specimens showed a relatively low infiltration of FoxP3 positive cells and CD206 positive cells, indicating that a low infiltration of regulatory T-cells and M2 macrophages took place. Remarkably, the patients from which these specimens were obtained lived considerably longer than other patients. Hence, it is fair to conclude that the Thorr02 and Thorr03 cell lines are particularly suitable for preparing a lysate for use in immunotherapy. After all, having pulsed dendritic cells with such a lysate that contains tumor antigens will stimulate a strong immune-response, while the absence of tumor-derived factors that induce immunosuppressive are limited.

Preferably three, more preferably five, most preferably all these cell lines are used for preparing the lysates according to the invention. It is particularly preferred to use at least the cell lines Thorr03 and Thorr02 for preparing a lysate according to the present invention, as these cell lines show a remarkably high immune stimulation of the T-cells in patients suffering from mesothelioma. These tumor cells thus express specific antigens that arouse the immune system to respond to the tumor. These antigens are present in the lysate and when loaded onto dendritic cells provoke anti-tumor responses by T cells.

Necrosis of the allogeneic mesothelioma tumor cells, can be achieved by methods commonly known in the prior art. However, subjecting the cells to freeze thawing cycles is particularly preferred. Preferably, the cells are made necrotic and lysed by freezing at temperatures below-70 degrees Celsius and thawing at temperatures of more than 30 degrees Celsius, particularly freezing is preferred at temperatures below −75 degrees Celsius and thawing is preferred at temperatures of more than 35 degrees Celsius and most preferred are temperatures for freezing below −80 degrees Celsius and temperatures for thawing of more than 37 degrees Celsius. It is also preferred that said freezing/thawing is repeated for at least 1 time, more preferably for at least 2 times, even more preferred for at least 3 times, particularly preferred for at least 4 times and most preferred for at least 5 times.

Preferably the tumor cells are treated with at least 50 Gy irradiation, preferably at least 100 Gy irradiation. This way it is avoided that any of the tumor cells remains viable. The irradiation treatment can be carried out before or after the tumor cells have been subjected to freezing and thawing.

It may also be advantageous to induce apoptosis in the allogeneic mesothelioma tumor cells. This can be achieved by subjecting the tumor cells to at least 15 $kJ/m^2$ UVB irradiation. After having induced apoptosis the apoptotic cells are lysed.

In order to make sure that the tumor cells are no longer viable the lysate of necrotic or apoptotic tumor cells is preferably subjected to at least 50 Gy, more preferably 100 Gy ionizing radiation. It is further preferred to centrifuge the lysate before or after irradiation.

A second aspect of the present invention relates to a lysate obtainable by the method described above. Lysates based on allogeneic mesothelioma tumor cells from two or more different mesothelioma cell-lines have not been reported before.

Particularly, lysates prepared from a mixture of at least three allogeneic mesothelioma tumor cell-lines, preferably at least four, more preferably at least five different allogeneic mesothelioma tumor cell-lines have not been reported before. Using lysates from such mixtures is advantageous for reasons that they provide a broader antigenic repertoire of tumor associated antigens (wide variety of potential tumor antigens), which will increase the ability of immune responses to recognize and destroy tumor cells because the opportunities to escape immune surveillance by modulation of antigen expression are more limited.

It is particularly preferred that the cell lysate is prepared from two or more of the following human cell lines, which have been deposited with the DSMZ. The cell lines were given the following codes and accession numbers: Thorr 01 (deposit No. DSM ACC3191), Thorr 02 (deposit No. DSM ACC3192), Thorr 03 (deposit No. DSM ACC3193), Thorr 04 (deposit No. DSM ACC3194), Thorr 05 (deposit No. DSM ACC3195), Thorr 06 (deposit No. DSM ACC3196).

It is particularly preferred to use at least the cell lines Thorr03 and Thorr02 for preparing a lysate according to the present invention.

The deposit was made pursuant to the terms of the Budapest treaty on the international recognition of the deposit of micro-organisms for purposes of patent procedure. Preferably three, more preferably five, most preferably all these cell lines are used for preparing the lysates according to the invention.

The use of tumor cell lysates from allogeneic mesothelioma tumor cells, also provides a more standardized lysate, bypassing the need for an individually prepared autologous tumor lysate.

A major advantage of the allogeneic approach over autologous is also that the tumor cell cells can be optimized, stored in bulk, and manufacturing/quality control timeliness shall not impact on the immediate disease progression of the patient as supply already exists.

If desired containers comprising the lysate as such can be brought on the market. Suitable containers for the lysate are hermetically sealed containers such as an ampoule or sachette, preferably indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The lysate may also be formulated into a pharmaceutical composition as will be described in more detail below.

A third aspect of the present invention relates to dendritic cells loaded (pulsed) with the lysate described above.

In accordance with the present invention the term "dendritic cells" has its conventional meaning and relates to antigen-presenting cells which capture antigens and have the ability to migrate to the lymph nodes and spleen, where they are particularly active in presenting the processed antigen to T cells. The term dendritic cells also encompasses cells which have an activity and function similar to dendritic cells. Dendritic cells can be derived from either lymphoid or mononuclear phagocyte lineages. Such dendritic cells can be found in lymphatic and non-lymphatic tissue. The latter appear to induce a T cell response only when being activated and having migrated to lymphatic tissues.

Dendritic cells are known to be the or amongst the most potent activators and regulators of immune responses. One important feature is that they are presently the only antigen presenting cells know to stimulate naïve T cells. Immature dendritic cells are characterized by their ability to take-up and process antigens, a function that is dramatically reduced in mature dendritic cells, which in turn exhibit enhanced presentation of processed antigens on their surface, mainly bound to MHC Class I and Class II molecules. Maturation is also associated with upregulation of co-stimulatory molecules (such as CD40, CD80 and CD86), as well as certain other cell surface proteins (e.g. CD83 and DC-Sign). Dendritic cell maturation is also usually associated with enhanced migratory capacity, resulting (in vivo) in migration of dendritic cells to the regional lymph nodes, where the dendritic cells encounter T and B lymphocytes.

Dendritic cells can be obtained from individuals, preferably humans, using methods known to those skilled in the art [14-17]. After having obtained the dendritic cells they are brought in culture and many more dendritic cells are obtained. Preferably, the dendritic cells cultured are autologous dendritic cells. The advantage of using autologous dendritic cells is that immune reactions of the patients against these dendritic cells is avoided and that the immunological reaction is triggered against the antigens from the mesothelioma tumor cells, which were present in the lysate.

Although using autologous dendritic cells provides many advantages, it may also be advantageous to use allogeneic dendritic cells. One of the major advantages of using autologous dendritic cells is that a medicament can be provided to patients that is ready to use. In other words one does not have to harvest, culture and load the dendritic cells from an individual but one can immediately administer the loaded allogeneic dendritic cells. This saves patient's valuable time.

Dendritic cells or their precursors are differentiated using suitable growth factors and/or cytokines, e.g. GM-CSF and IL-4, the resulting immature dendritic cells are loaded with a lysate according to the invention. Immature dendritic cells loaded with a lysate according to the invention are further maturated to mature dendritic cells. In special cases also mature dendritic cells can be loaded (pulsed) with antigens or immunogens from the lysate.

Preferably, the dendritic cells are loaded with at least 0.1 tumor cell equivalents per dendritic cell, preferably at least 0.2 tumor cell equivalents per dendritic cell, more preferably at least 0.5 tumor cell equivalents per dendritic cell, most preferably at least one tumor cell equivalent per dendritic cell.

The dendritic cells used are preferably derived from vertebrates, preferably from a mammal, most preferably from humans.

A fifth aspect of the present invention relates to pharmaceutical compositions comprising the lysate according to the present invention, or to pharmaceutical compositions comprising dendritic cells loaded with the lysate according to the present invention in combination with a pharmaceutically acceptable carrier.

In accordance with the present invention the term "pharmaceutical composition" relates to compositions comprising the cell lysates or dendritic cells loaded with the lysate as described hereinabove. Such pharmaceutical compositions comprise a therapeutically effective amount of the cell lysates or dendritic cells of the present invention, and a pharmaceutical acceptable carrier.

Preferably, a dosage of the composition administered to a patient comprises $1*10^3$ to $1*10^{10}$ loaded dendritic cells, preferably $1*10^5$ to $1*10^9$ loaded dendritic cells, most preferably $1*10^6$ to $1*10^8$ loaded dendritic cells. Preferably these dendritic cells comprise at least 0.1 tumor cell equivalent per dendritic cell, more preferably at least 0.2 tumor cell equivalents per dendritic cell, even more preferably at least 0.5 tumor cell equivalents per dendritic cell, most preferably at least one tumor cell equivalents per dendritic cell. Most preferably a dosage of the pharmaceutical composition comprises $1*10^3$ to $1*10^{10}$ dendritic cells loaded with at least 1 tumor cell equivalent per dendritic cell.

This pharmaceutical composition may be administered with a physiologically acceptable carrier to a patient, as described herein. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

These pharmaceutical compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutical effective amount of the cell lysate, preferably in purified form, together with a suitable amount of carrier so as to provide the form for proper administration to the patient. The formulation should suit the mode of administration.

In another preferred embodiment, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The cell lysate of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The precise dose of the cell lysate or loaded dendritic cells to be employed in the formulation will depend on the route of administration, and state of the disease, and should be decided according to the judgment of the practitioner and each patient's circumstances.

Preferably, the pharmaceutical composition is formulated such that it is suitable for acting as a vaccine. The forms or methods for manufacturing vaccine compositions according to the present invention are not particularly limited, and a composition in a desired form can be prepared by applying a single method available in the field of the art or methods in an appropriate combination. For the manufacture of a vaccine composition, aqueous media such as distilled water for injection and physiological saline, as well as one or more kinds of pharmaceutical additives available in the field of the art can be used. For example, buffering agents, pH adjusting agents, solubilizing aids, stabilizing agents, soothing agents, antiseptics and the like can be used, and specific ingredients thereof are well known to those skilled in the art. The composition can also be prepared as a solid preparation such as a lyophilized preparation, and then prepared as an injection by adding a solubilizing agent such as distilled water for injection before use. Depending upon the manner of introduction, the compounds may be formulated in a variety of ways as discussed below. The concentration of therapeutical active compound in the formulation may vary from about 0.1-100 wt %.

The pharmaceutical composition according to the present invention may be administered alone or in combination with other treatments, i.e., radiation, or other chemotherapeutic agents or anti-cancer agents, such as a therapeutically effective amount of nitrogen mustard alkylating agents, nitrosoureas, alkyl sulfonates, temozolomide (Temodal®) or COX-2 inhibitors, preferably nitrogen mustard alkylating agents, such as cyclophosphamide (Endoxan®), Chlorambucil (Leukeran®), mechorethamine (Mustardgen®), uramustine, melphalan (Alkeran®) or Ifosfamide.

In a preferred embodiment, the compositions are in a water-soluble form, such as pharmaceutical acceptable salts, which is meant to include both acid and base addition salts.

The compositions can be prepared in various forms, such as injection solutions, tablets, pills, suppositories, capsules, suspensions, and the like.

Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

As said, the pharmaceutical composition according to the present invention, or the lysate or the dendritic cells according to the invention, preferably the pharmaceutical composition may be used in combination with an adjuvant.

With respect to the present invention the term "adjuvant" means that the natural ability of an antigen to induce an immune response can be modified, and in particular enhanced, by altering or by mixing it or loaded dendritic cells described hereinabove with another substance. The term "adjuvant" also means that tumor cells from which the lysates are generated and/or dendritic cells are genetically modified in order to express adjuvants or other factors which influence the immune response, as for example costimulatory factors. The procedure or the substance used to enhance immune responses is called an adjuvant. At least three classes of adjuvants have been used for a long time; these are mineral oil emulsions, aluminium compounds, and surface active materials such as saponin, lysolecithin, retinal, Quil A. RTM., some liposomes, and pluronic polymer formulations. See, for example, Fundamental Immunology, edited by William E. Paul, at p. 1008, Raven Press, New York (this book will hereinafter be referred to as "Fundamental Immunology"). Aluminium adjuvants used alone or in combination include aluminium hydroxide gel, aluminium phosphate, aluminium sulphate, and alums comprising ammonium alum (such as (NH. sub. 4). sub. 2 SO. sub. 4. Al. sub. 2 (SO. sub. 4). sub. 3) and potassium alum. Aluminium hydroxide (hereinafter "AL") is one of the older adjuvants and it is considered so safe that it has been applied in bacterial and viral vaccines administered to billions of people around the world. Calcium phosphate gel (hereinafter "CP") has similar properties and is also used in vaccines. Both substances are available in pharmaceutical qualities in most countries worldwide.

Techniques for preparing adjuvant-antigen preparations for injection are well known in the art. See, for example, Terry M. Philips, Analytical Techniques in Immunochemistry, pp. 307-10, Marcel Dekker, New York, 1992. Other adjuvants include complete Freund's adjuvant (a water-in-oil emulsion in which killed, dried, mycobacteria—usually *M tuberculosis*—are suspended in the oil phase); incomplete Freund's adjuvant (analogous to the complete Freund's adjuvant with no mycobacteria); ISCOM (or immune stimulating complex, comprising lipophilic particles formed by the spontaneous association of cholesterol, phospholipid and the saponin Quil A. RTM.); lipopolysaccharide (complex molecules consisting of a lipid core—lipid A—with a polysaccharide side chain that are components of certain bacilli, Lipid A is incorporated into the outer membrane of the bacterium and the polysaccharide projects extracellularly. Their adjuvant potency is associated with lipid A; they are also mitogenic for murine B lymphocytes); and mycobacterial adjuvants (whole, heat killed, dried, mycobacteria-such as *M. tuberculosis, M. avium, M. phlei*, and *M. smeg-*

*matis*) that, when suspended in mineral oil and emulsifier, have adjuvant activity with respect to any antigen given with them.

Extracts of some mycobacteria, e.g., mycobacterial peptidoglycolipids have similar adjuvant activities. See, for example, Dictionary of Immunology at pp. 3, 7, 46, 94, 97, 105, and 116; R. B. Luftig, Microbiology and Immunology, pp. 228-29, Lippincott-Raven Publishers, Philadelphia 1998. Microbial adjuvants include *Corynebacterium parvum* and *Bordetella pertussis*. See, for example, Handbook of Immunology at 115-16. Use of controlled-release preparations and materials with adjuvant activity and possible sites of action have been described in Fundamental Immunology at pp. 1007-09. Mineral carriers such as aluminium hydroxide, potassium ammonium sulphate, and potassium aluminium sulphate adsorb the antigen on their surface. These common adjuvants have been used at a 0.1% concentration with up to 1 mg protein antigen in 1 mi administered to animals at doses of 0.2-0.5 mu/(kg body weight). See Miroslav Ferencik, Handbook of Immunochemistry, p. 115, Chapman & Hall 1993 (this book will hereinafter be referred to as "Handbook of Immunochemistry"). Although Freund's adjuvant is toxic and not used for immunization of human beings, mineral adjuvants such as aluminium hydroxide are common in human medicine. 1d. at 116. In addition to alum, other adjuvants in the group of inert carriers include bentonite, latex, and acrylic particles. See Fundamental Immunology at 1008. Combinations of adjuvants can also have adjuvant properties. For example, it has been shown that the combination of saponin and muramyl dipeptide in a squalene in water emulsion is superior to alum as an adjuvant for inducing certain responses in mice. R. Bomford, M. Stapleton, S. Wilson, A. McKnight, and T. Andronova, The control of the antibody isotype responses to recombinant human immunodeficiency virus gp120 antigen by adjuvants, AIDS Res. Hum. Retroviruses Vol. 8 (1992) pp. 1765 et seq. These adjuvants are complemented by new adjuvants that have been developed during the last fifteen years. See, for example, Anthony C. Allison, The Role of cytokines in the Action of Immunological Adjuvants, in Vaccine Design. The Role of cytokine Networks, edited by Gregory Gregoriadis and Brenda McCormack, NATO ASI Series A: Life Sciences Vol 293, pp. 1-9, Plenum Press, New York 1997 (this book will hereinafter be referred to as "Vaccine Design"); Immunology at p. 116; H. Snippe, I. M. Fernandez and C. A. Kraaijeveld, Adjuvant Directed Immune Specificity at the Epitope Level. Implications for Vaccine Development. A Model Study Using Semliki Forest Virus Infection of Mice, in Vaccine Design at pp. 155-73.

An adjuvant can be administered prior to, simultaneously with, or following the administration of the antigen. Antibody production enhancement caused by adjuvants is not fully understood. However, adjuvant properties that may exist either alone or in various combinations and which permit a substance or formulation to be described as adjuvant active have been defined. See, for example, J. C. Cox and A. R. Coulter, Adjuvants—A classification and review of their modes of action, Vaccine Vol. 15 (1981) pp. 248 et seq.; John Cox, Alan Coulter, Rod Macfarlan, Lorraine Beezum, John Bates, Tuen-Yee Wong and Debbie Drane, Development of an Influenza-ISCOM. TM. Vaccine, in Vaccine Design at pp. 33-49. One of these properties is depot generation, whereby the vaccine is retained near the dose site to give short-term trickle release or a longer term pulsed release. Id. at p. 34.

Preferably, the pharmaceutical or vaccine composition is administered directly or in combination with an adjuvant mentioned herein above or loaded on antigen presenting cells, particularly dendritic cells. It is also preferred that both the pharmaceutical or vaccine composition and the adjuvant and the pharmaceutical or vaccine composition and the loaded dendritic cells are administered together or separately from each other e.g. at different time points or at different locations.

Additionally, it is also preferred that said pharmaceutical composition and adjuvant is administered together with said pharmaceutical composition loaded on dendritic cells. Since dendritic cells are highly specialized antigen-presenting cells with the unique capability in initiating and regulating antigen-specific immune responses, it is preferred to combine them with the pharmaceutical compositions of the present invention.

A sixth aspect of the present invention relates to a method for preparing a pharmaceutical composition for use in the treatment or prevention of mesothelioma, comprising the steps of:

i) providing allogeneic mesothelioma tumor cells from at least two different cell lines, and preparing a lysate thereof;
ii) providing dendritic cells;
iii) loading the dendritic cells with the lysate of the tumor cells.

A pharmaceutically acceptable carrier may be added before, during or after loading the dendritic cells with the lysate. However, also the lysate itself or the culture medium of the dendritic cells may be regarded as a pharmaceutically acceptable carrier.

Preferably, the lysate used in the method described above is the lysate as prepared in the previous paragraph, i.e. a lysate obtained from necrotic or apoptotic mesothelioma tumor cells.

The dendritic cells to be loaded with the lysate can be autologous or allogeneic. However, it is preferred to use autologous dendritic cells. It is further preferred to load immature dendritic cells, although mature dendritic cells may also be used.

The lysate, the loaded dendritic cells and the pharmaceutical compositions thereof according to the invention may be used for treating patients suffering from mesothelioma, or may be administered to person having increased chances for developing mesothelioma.

The lysate, the loaded dendritic cells or the pharmaceutical composition according to the present invention may be administered to patients in combination with a therapeutically effective amount of other pharmaceutically active compounds, such as nitrogen mustard alkylating agents, nitrosoureas, alkyl sulfonates, temozolomide (Temodal®) or COX-2 inhibitors, preferably nitrogen mustard alkylating agents, such as cyclophosphamide (Endoxan®), Chlorambucil (Leukeran®), mechorethamine (Mustardgen®), uramustine, melphalan (Alkeran®) or Ifosfamide. Such combinations may be formulated as a kit. However, it is particularly preferred to prepare a fixed dose combination.

It is further preferred that patients are administered per vaccination $1*10^3$ to $1*10^{10}$ loaded dendritic cells, preferably $1*10^5$ to $1*10^9$ loaded dendritic cells, most preferably $1*10^6$ to $1*10^8$ loaded dendritic cells.

Preferably these dendritic cells comprise at least 0.1 tumor cell equivalents per dendritic cell, more preferably at least 0.2 tumor cell equivalents per dendritic cell, even more preferably at least 0.5 tumor cell equivalents per dendritic cell, most preferably at least one tumor cell equivalent per dendritic cell.

It is particularly preferred to administer these dosages at least twice, more preferably at least three times, and most preferably at least five times. It is particularly preferred to administer to a patient in need thereof at least three times a dosage of $1*10^3$ to $1*10^{10}$ dendritic cells loaded with at least 1 tumor cell equivalent per dendritic cell.

The invention will be described further by the following non-limiting examples.

A last aspect of the present invention relates to the following human cell lines Thorr 01 (deposit No. DSM ACC3191), Thorr 02 (deposit No. DSM ACC3192), Thorr 03 (deposit No. DSM ACC3193), Thorr 04 (deposit No. DSM ACC3194), Thorr 05 (deposit No. DSM ACC3195), Thorr 06 (deposit No. DSM ACC3196). These cells are able to divide without losing their antigenic properties.

EXAMPLES

Example 1 (Allogeneic Tumor Lysate)

Experiments have been carried out to generate tumor-specific immunity by loading (pulsing) dendritic cells with allogeneic tumor lysates in a murine model for mesothelioma. The mice used in this study were injected with autologous AB1 mesothelioma cell lines, such that mesothelioma would develop from these cells. Each condition was tested in at least a group of 4 mice in two independent experiments.

I. Dendritic Cell Preparation

Dendritic cells (DC) were generated from bone marrow-derived monocytes with specific growth factors. To obtain bone marrow from healthy BALB/c or CBA/j donor mice, femur and tibia bones were collected, broken and washed with alcohol. Culture medium was added and cells were filtered over 100 μm membrane. Next osmotic lysis buffer (2 ml) was added to remove erythrocytes and afterwards cell counting was done. We used 100-mm Petri dishes, each dish with $10 \times 10^6$ cells in 10 ml DC-tissue culture medium (DC-TCM). DC-tissue culture medium exists of RPMI 1640 medium (Invitrogen) containing Glutamax-I (Invitrogen) supplemented with 5% FBS, 50 μg/ml gentamycin, 50 μM beta-mercaptoethanol (Sigma-Aldrich) and 20 ng/ml recombinant murine granulocyte macrophage-colony-stimulating factor (GM-CSF). Cells were cultured at 37° C. in a humidified atmosphere at 5% $CO_2$. At day 3, we added 10 ml of fresh DC-TCM to each Petri dish. On day 6, 10 ml of each dish was replaced with 10 ml of fresh DC-TCM. After days 8 of culture, each Petri dish contained $30 \times 10^6$ immature dendritic cells (iDCs).

II. Loading of Dendritic Cells with Tumor Lysate

Immature dendritic cells (iDC) were then stimulated with allogeneous tumor lysate. To load iDC, tumor lysate was added in a ratio of 3 tumor cell equivalents per 1 iDC. AC29 cell line derived tumor lysate was prepared from $50 \times 10^6$ AC29 cells suspended per ml PBS. Since the AB 1 cell line was used to induce the mesothelioma tumor growth in the mice, the AC29 mesothelioma cell line is considered an allogeneic tumor lysate when administered to the mice suffering from AB 1 cell line induced mesothelioma.

The cell suspension was frozen in liquid nitrogen and disrupted by four cycles of freeze-thawing followed by sonication for four times during 10 seconds with an amplitude of 10 microns, using a Soniprep 150 ultrasonic disintegrator (Sanyo Gallenkamp BV, Breda, The Netherlands) on ice. This procedure was done for untreated and heat+UV treated tumor cells to produce necrotic and apoptotic tumor cell lysate. Tumor cell lysate was stored at −80° C. until use.

The cell cultures of iDCs from BALB/c and CBA/j mice with AC29 tumor cell lysate were kept for 8 hours at 37° C. After 8 hours, 100 μg/ml Lipopolysaccharide (LPS) [E. coli 026:B6, Sigma-Aldrich] was added to the DC culture to allow complete maturation while incubated overnight at 37° C. The next day, DCs were collected by addition of PBS to separate DCs from the dish by gentile pipetting. DCs were washed in PBS at 400×g for 7 min with a Varifuge 3.OR centrifuge (Heraeus intstruments) at 4° C. and resuspended in 2 ml PBS. Next DCs were separated and purified from tumor cell lysate and debris using 3 ml Lympholyte-Mammal (Cedarlane, Hornby, ON, Canada) density gradient centrifugation. Then, after centrifugation at 1200×g (Heraeus Instruments) for 20 min at room temperature, DCs were collected from the interpase using a pipette. Again cells were washed in PBS at 400 rpm for 7 min. at 4° C. The cells were resuspended to a concentration of $3 \times 10^6$ viable DCs in 500 μl PBS. The quality of the DC preparation was determined by cell counting, morphologic analysis and cell surface expression.

III. Administration of Loaded Dendritic Cells to Mice Suffering from Mesothelioma Dendritic cells loaded with AC29 cell lysate were injected intraperitoneally in either BALB/c or CBA/J mice 14 and 7 days prior to a lethal tumour injection (protective setting) or 1 and 8 days after tumour injection (therapeutic setting). At least 4 mice per group/condition were used. The occurrence of tumour growth, body weight, physical well-being, and survival was measured for two months. The spleen and tumour material from surviving mice were collected and analysed for their lytic activity in a chromium-release assay and by flowcytometry (Granzyme B and IFN-gamma positive cells).

IV. Results

Figure 1:
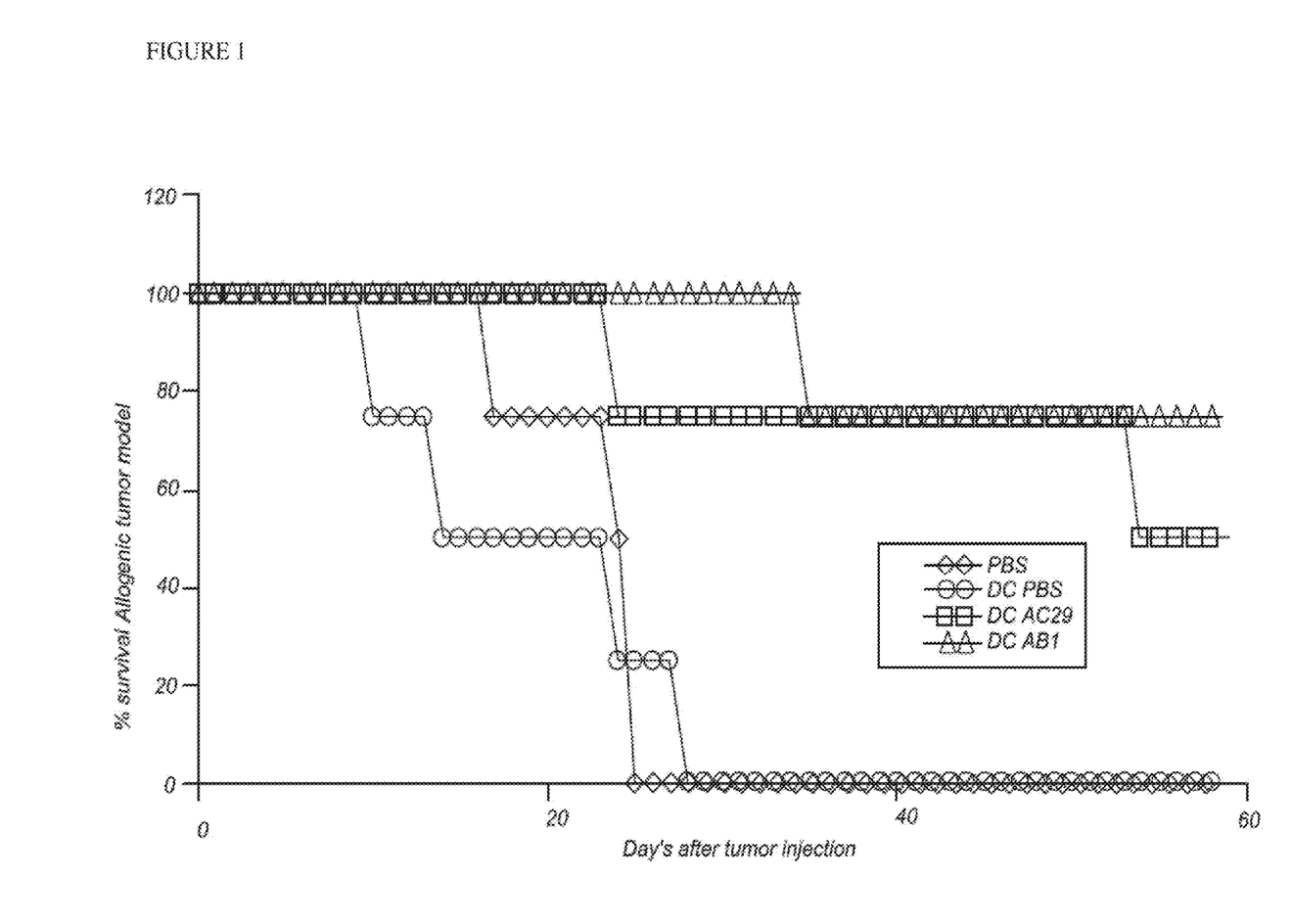
FIG. 1 shows the survival rate of survival rate of mice treated with allogeneic DC-based immunotherapy compared to untreated mice.
Figure 2:
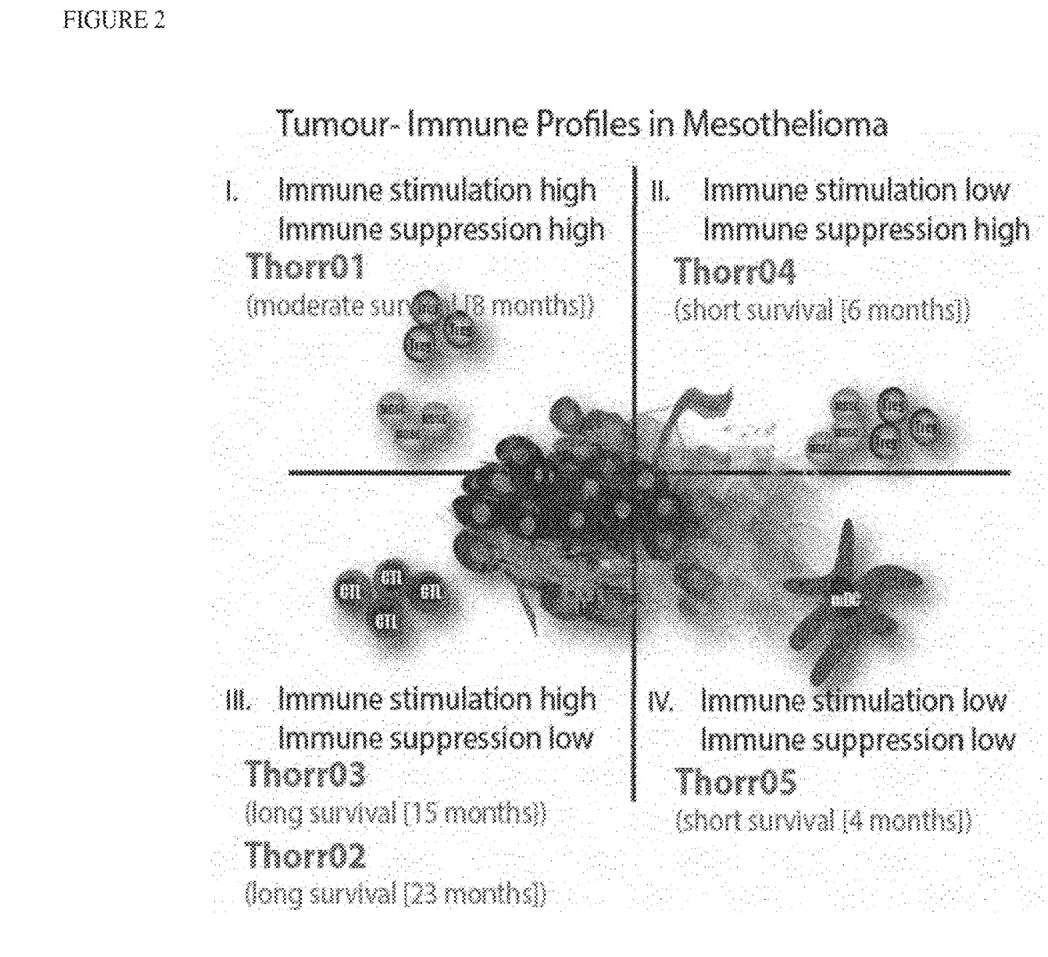
FIG. 2 provide tumor-immune profiles in mesothelioma.

Allogeneic DC-based immunotherapy showed an increased survival rate of the treated mice compared to untreated mice, as is shown in FIG. 1. Besides an increase in the amount of CD8 positive cytotoxic T cells, the percentage of IFN-gamma and granzyme B production per cell was higher in allogeneic DC treated mice compared to non-treated mice. The killing capacity of splenocytes from 'allogeneic' treated mice were highly increased when cells were co-cultured with chromium labelled AC29 tumour cells.

Example 2: (Autologous Tumor Lysate)

The same protocol as mentioned above with respect to the allogeneic tumor lysate was followed with an autologous tumor lysate, i.e. AB 1 mouse mesothelioma cell lines. The mesothelioma cell lines used to prepare the lysate (i.e. AB 1 cell line) was the same as the cell line used to induce mesothelioma in the mice. Hence, the lysate was considered autologous. Again the treated mice showed an improved survival rate compared to untreated mice. The survival rate of the mice treated with the autologous tumor cell lysate (AB 1) loaded dendritic cells was comparable to the mice treated with the allogeneic tumor cell lysate (AC29) loaded dendritic cells. Each condition was tested in at least 4 mice per experiment. Each experiment was performed twice.

Example 3 the Origin of the Preferred Cell-Lines Thorr01 to Thorr06

Malignant mesothelioma is characterized by distinctive tumour- and immune-profiles. There is a marked heterogeneity and individuality of immune infiltration into the tumour that correlate with lymph node involvement and tumour behavior (invasive, aggressive, moderate and indolent). There are 4 possible immune-oncology characteristics, based on balances between immune activation and immune suppression. The cell-lines Thorr01-06 as claimed in the present invention have been derived from tumor tissue, at least one cell line from one of the 4 immune-oncology characteristics. The characteristics of the tumor from which cell lines were generated are shown below:

Thorr01 cell-line has been derived from a mesothelioma tumor tissue having:
- more than 500 $CD3^+$ cells per $mm^2$;
- more than 200 $CD45RO^+$ cells per $mm^2$;
- more than 50 $FoxP3^+$ cells per $mm^2$; and
- more than 1000 $CD206^+$ cells per $mm^2$.

Thorr02 cell-line has been derived from a mesothelioma tumor tissue having:
- more than 500 $CD3^+$ cells per $mm^2$;
- more than 200 $CD45RO^+$ cells per $mm^2$;
- less than 50 $FoxP3^+$ cells per $mm^2$; and
- less than 1000 $CD206^+$ cells per $mm^2$.

Thorr03 cell-line has been derived from a mesothelioma tumor tissue having:
- more than 500 $CD3^+$ cells per $mm^2$;
- more than 200 $CD45RO^+$ cells per $mm^2$;
- less than 50 $FoxP3^+$ cells per $mm^2$; and
- less than 1000 $CD206^+$ cells per $mm^2$.

Thorr04 cell-line has been derived from a mesothelioma tumor tissue having:
- less than 500 $CD3^+$ cells per $mm^2$;
- less than 200 $CD45RO^+$ cells per $mm^2$;
- more than 50 $FoxP3^+$ cells per $mm^2$; and
- more than 1000 $CD206^+$ cells per $mm^2$.

Thorr05 and Thorr06 cell lines have been derived from a mesothelioma tumor tissue having:
- less than 500 $CD3^+$ cells per $mm^2$;
- less than 200 $CD45RO^+$ cells per $mm^2$;
- less than 50 $FoxP3^+$ cells per $mm^2$; and
- less than 1000 $CD206^+$ cells per $mm^2$.

It is thus advantageous to prepare a lysate from two or more of said cell-lines for loading dendritic cells. At least two cell lines but preferable at least four cell lines, one out of each quadrant to provide all different immune-tumoural characteristics of mesothelioma, are selected for the widest variety of antigenically tumour-associated antigen (TAA) source. These TAA are taken up by autologous DC ex vivo and then presented in the context of appropriate MHC alleles to T cells in patients after vaccination.

REFERENCES

1. Steinman, R. M. and M. C. Nussenzweig, *Dendritic cells: features and functions*. Immunol Rev, 1980. 53: p. 127-47.
2. Banchereau, J. and R. M. Steinman, *Dendritic cells and the control of immunity*. Nature, 1998. 392(6673): p. 245-52.
3. Steinman, R. M. and M. Dhodapkar, *Active immunization against cancer with dendritic cells: the near future*. Int J Cancer, 2001. 94(4): p. 459-73.
4. Della Bella, S., et al., *Altered maturation of peripheral blood dendritic cells in patients with breast cancer*. Br J Cancer, 2003. 89(8): p. 1463-72.
5. Hartmann, E., et al., *Identification and functional analysis of tumor-infiltrating plasmacytoid dendritic cells in head and neck cancer*. Cancer Res, 2003. 63(19): p. 6478-87.
6. Huang, A., et al., *Increased serum transforming growth factor-beta1 in human colorectal cancer correlates with reduced circulating dendritic cells and increased colonic Langerhans cell infiltration*. Clin Exp Immunol, 2003. 134(2): p. 270-8.
7. Lee, J. R., et al., *Pattern of recruitment of immunoregulatory antigen-presenting cells in malignant melanoma*. Lab Invest, 2003. 83(10): p. 1457-66.
8. Anderson, N. L. and N. G. Anderson, *The human plasma proteome: history, character, and diagnostic prospects*. Mol Cell Proteomics, 2002. 1(11): p. 845-67.
9. Chang, A. E., et al., *A phase I trial of tumor lysate-pulsed dendritic cells in the treatment of advanced cancer*. Clin Cancer Res, 2002. 8(4): p. 1021-32.
10. Enk, A. H., et al., *Dendritic cells as mediators of tumor-induced tolerance in metastatic melanoma*. Int J Cancer, 1997. 73(3): p. 309-16.
11. Zhao, X., Y. Q. Wei, and Z. L. Peng, *Induction of T cell responses against autologous ovarian tumors with whole tumor cell lysate-pulsed dendritic cells*. Immunol Invest, 2001. 30(1): p. 33-45.
12. Cranmer, L. D., K. T. Trevor, and E. M. Hersh, *Clinical applications of dendritic cell vaccination in the treatment of cancer*. Cancer Immunol Immunother, 2004. 53(4): p. 275-306.
13. Hegmans, J. P., et al., *Immunotherapy of Murine Malignant Mesothelioma Using Tumor Lysate-pulsed Dendritic Cells*. Am J Respir Crit Care Med, 2005. 171(10): p. 1168-77.
14. Hegmans, J. P., et al., *Consolidative Dendritic Cell-Based Immunotherapy Elicits Cytotoxicity Against Malignant Mesothelioma*. Am J Respir Crit Care Med, 2010.
15. Banchereau, J. and A. K. Palucka, *Dendritic cells as therapeutic vaccines against cancer*. Nat Rev Immunol, 2005. 5(4): p. 296-306.
16. Berger, T. G., et al., *Efficient elutriation of monocytes within a closed system (Elutra) for clinical-scale generation of dendritic cells*. J Immunol Methods, 2005. 298(1-2): p. 61-72.
17. de Vries, I. J., et al., *Phenotypical and functional characterization of clinical-grade dendritic cells*. Methods Mol Med, 2005. 109: p. 113-26.

The invention claimed is:

1. An immunogenic lysate comprising lysed allogeneic mesothelioma tumor cells from at least two different cell lines selected from the group consisting of Thorr 01 (deposit No. DSM ACC3191), Thorr 02 (deposit No. DSM ACC3192), Thorr 03 (deposit No. DSM ACC3193), Thorr 04 (deposit No. DSM ACC3194), Thorr 05 (deposit No. DSM ACC3195), and Thorr 06 (deposit No. DSM ACC3196).

2. The immunogenic lysate according to claim 1, wherein the mesothelioma tumor cells comprise cells from at least three different cell lines selected from the group consisting of Thorr 01 (deposit No. DSM ACC3191), Thorr 02 (deposit No. DSM ACC3192), Thorr 03 (deposit No. DSM ACC3193), Thorr 04 (deposit No. DSM ACC3194), Thorr 05 (deposit No. DSM ACC3195), and Thorr 06 (deposit No. DSM ACC3196).

3. The immunogenic lysate according to claim 1, wherein the lysate or the tumor cells are treated with at least 50 Gy irradiation.

4. A pharmaceutical composition, comprising the lysate according to claim 1 and a pharmaceutically acceptable carrier.

5. The pharmaceutical composition according to claim 4, wherein the composition comprises an adjuvant.

6. The pharmaceutical composition according to claim 5, wherein the adjuvant comprises heat-shock protein, Bacillus Calmette-Geurin (BCG), bacterial non-methylated DNA containing one or more CpG-ODN sequences, Detox or Montanide.

7. A method of treating mesothelioma in a patient in need thereof, comprising administering to the patient a lysate according to claim 1.

8. The method according to claim 7, wherein the lysate is administered to the patient in combination with a therapeutically effective amount of a nitrogen mustard alkylating agent, nitrosourea, alkyl sulfonate, or COX-2 inhibitor.

9. The method according to claim 7, wherein the patient receives surgery and/or chemotherapy treatment prior to administration of the lysate.

10. A method of treating mesothelioma in a patient in need thereof, comprising administering to the patient a pharmaceutical composition according to claim 4.

11. The method according to claim 10, wherein the composition is administered to the patient in combination with a therapeutically effective amount of a nitrogen mustard alkylating agent, nitrosourea, alkyl sulfonate, or COX-2 inhibitor.

12. The method according to claim 11, wherein the patient receives a chemotherapy treatment prior to administration of the composition.

* * * * *